(12) United States Patent
Hamelin et al.

(10) Patent No.: US 7,214,941 B2
(45) Date of Patent: May 8, 2007

(54) CRACK DETECTION IN RAZOR BLADES

(75) Inventors: Michel Hamelin, West Roxbury, MA (US); William Masek, North Attleboro, MA (US); Joseph A. Depuydt, Quincy, MA (US)

(73) Assignee: The Gillette Company, Boston, MA (US)

( * ) Notice: Subject to any disclaimer, the term of this patent is extended or adjusted under 35 U.S.C. 154(b) by 249 days.

(21) Appl. No.: 11/014,366

(22) Filed: Dec. 16, 2004

(65) Prior Publication Data

US 2006/0192123 A1    Aug. 31, 2006

(51) Int. Cl.
*G01J 5/02*    (2006.01)

(52) U.S. Cl. .................................... 250/341.1

(58) Field of Classification Search .............. 250/341.1
See application file for complete search history.

(56) References Cited

U.S. PATENT DOCUMENTS

| | | | |
|---|---|---|---|
| 1,897,141 A * | 2/1933 | Peters ..................... 324/71.1 |
| 2,073,832 A * | 3/1937 | Godfrey .................... 209/702 |
| 2,124,579 A | 7/1938 | Knerr et al. |
| 2,855,564 A | 10/1958 | Irwin et al. |
| 3,538,433 A | 11/1970 | Wood et al. |
| 3,619,770 A | 11/1971 | Forster |
| 3,693,075 A | 9/1972 | Forster |
| 3,753,085 A | 8/1973 | Morton et al. |
| 3,875,502 A | 4/1975 | Neumaier |
| 4,325,026 A | 4/1982 | Cooper, Jr. et al. |
| 4,598,206 A | 7/1986 | Nelson |
| 4,659,991 A | 4/1987 | Weischedel |
| 4,673,879 A | 6/1987 | Harris et al. |
| 4,806,894 A | 2/1989 | Koto |
| 5,041,786 A | 8/1991 | Takaishi et al. |
| 5,066,891 A | 11/1991 | Harrold et al. |
| 5,069,005 A * | 12/1991 | Hovland et al. .............. 451/53 |
| 5,111,048 A | 5/1992 | Devitt et al. |
| 5,311,127 A | 5/1994 | Bisiaux |
| 5,424,640 A | 6/1995 | Levy |
| 5,451,872 A | 9/1995 | Antonine et al. |
| 5,621,323 A * | 4/1997 | Larsen ..................... 324/318 |
| 5,638,000 A | 6/1997 | Forster |
| 5,669,156 A | 9/1997 | Vejchoda |
| 5,793,205 A | 8/1998 | Griffith et al. |

(Continued)

FOREIGN PATENT DOCUMENTS

DE    199 51 172 A1    4/1975

(Continued)

OTHER PUBLICATIONS

XP008061570, Oct. 30, 1930, H. R. Simonds.

(Continued)

*Primary Examiner*—David Porta
*Assistant Examiner*—Christine Sung
(74) *Attorney, Agent, or Firm*—Fish & Richardson P.C.

(57) ABSTRACT

Methods are provided for determining the presence of cracks in razor blades during manufacturing. The methods may include, for example, providing a plurality of razor blades in a stack, inducing a current in the stack, and measuring a parameter that is related to the current and indicative of the presence or absence of cracks in the razor blades.

25 Claims, 3 Drawing Sheets

U.S. PATENT DOCUMENTS

| | | | |
|---|---|---|---|
| 5,914,595 A | 6/1999 | Piriou et al. | |
| 5,926,020 A | 7/1999 | Samson | |
| 5,942,893 A | 8/1999 | Terpay | |
| 5,990,677 A | 11/1999 | Goldfine et al. | |
| 6,046,764 A * | 4/2000 | Kirby et al. | 348/92 |
| 6,084,404 A | 7/2000 | Jiles et al. | |
| 6,144,206 A | 11/2000 | Goldfine et al. | |
| 6,146,086 A | 11/2000 | Snell et al. | |
| 6,150,809 A | 11/2000 | Tiernan et al. | |
| 6,215,300 B1 | 4/2001 | Herron | |
| 6,291,992 B1 | 9/2001 | van Andel et al. | |
| 6,456,069 B1 | 9/2002 | Scarzello et al. | |
| 6,566,871 B2 | 5/2003 | Holzl | |
| 6,730,912 B2 | 5/2004 | Sun et al. | |
| 2002/0163333 A1 | 11/2002 | Schlicker et al. | |
| 2005/0002435 A1* | 1/2005 | Hashimoto et al. | 374/43 |

FOREIGN PATENT DOCUMENTS

| | | | |
|---|---|---|---|
| GB | | 390436 A | 4/1933 |
| GB | | 1405414 A | 9/1975 |

OTHER PUBLICATIONS

XP008061581, Nov. 1984, D. N. Upcott.

XP008061636, Jun. 1956, E. Altholz.

American Society for Nondestructive Testing, *Nondestructive Testing Handbook, vol. 3: Infrared and Thermal Testing*, Chapter 2, 2001.

Wullink, J and Darses, P. *On-line Thermography Applied to Crack Detection in Steel Billets*, Fifth conference on Quantiative Infra-Red Thermography (QIRT), Jul. 18-21, 2000, Reims, France.

Davies, E.J. *Conduction and Induction Heating*, IEE Power Engineering Series, #11, 1990 Peter Peregrinus publisher, Chapter 7.

Blitz, J. *Electrical and Magnetic Methods of Non-Destructive Testing*, Chapman-Hall 1991, p. 42.

* cited by examiner

CRACK DETECTION IN RAZOR BLADES

TECHNICAL FIELD

This invention relates to methods of detecting cracks in razor blades during a razor manufacturing process.

BACKGROUND

Razor blades are in many cases formed by a process involving heat treating and sharpening a continuous strip of perforated blade steel, and then breaking the strip into segments of the desired blade length. The resulting blades are then stacked on a spindle for further treatment, e.g., treating the blade edges with coatings to enhance durability and/or lubricity.

Such spindles typically contain a great many blades, for example up to 4000 blades, stacked so that their edges are parallel and their adjacent broad faces are in contact with each other. When the blades are arranged in this manner, it is difficult to inspect the blades for cracks. While other types of defects generally may be observed using machine vision or human observation, cracks tend to be difficult to detect due to the tendency of the weight of the stack to close up any cracks. Cracked or broken blades can be extremely difficult to detect visually when the fracture surfaces are aligned to their original position and the crack is closed without the presence of an air gap. In other industries, such cracks can be made visible with the use of dye penetrants. However, dye cannot be applied to the surface of a blade stack because the dye would penetrate between the blades and cause staining. The presence of interfaces between neighboring blades exacerbates the difficulty of detecting cracked blades, as these interfaces are generally indistinguishable from the targeted cracks using conventional nondestructive testing systems such as machine vision, ultrasonic inspection, or eddy current testing.

SUMMARY

The present invention provides automated methods for crack detection in a stack of razor blades.

In some methods, electrical current is induced with a high-frequency induction coil as an air "knife" fans the blades. Thermal images are recorded with an infrared camera while the blades become exposed to the electromagnetic field. If the proper current density and timing is reached, the presence of a crack will be revealed by an abnormal temperature gradient across the blade.

In one aspect of the invention, a method of inspecting razor blades for cracks includes providing a plurality of razor blades in a stack, inducing a current in the stack, and measuring a parameter that is related to the current and indicative of the presence or absence of cracks in the razor blades.

In another aspect of the invention, a method of inspecting razor blades for cracks includes providing a plurality of razor blades in a stack, inducing a current in the stack, and measuring infrared radiation emitted by the stack to determine the presence or absence of cracks in the razor blades.

The methods can include one or more of the following features.

In some embodiments, the inducing step includes placing an induction coil adjacent the stack and delivering alternating current to the coil. In certain embodiments, the inducing step includes placing the induction coil around the stack and causing relative movement between the induction coil and the stack in a direction parallel to a long axis of the stack.

In some embodiments, the measuring step includes measuring the temperature of at least one of the razor blades in the stack. In certain embodiments, the method further includes monitoring the measured temperature for localized areas of relatively higher temperature, indicative of cracks. In some embodiments, the method further includes obtaining a temperature map (e.g., a set of temperature profiles of the blades along the length of the stack).

In certain embodiments, the measuring step includes measuring infrared radiation emitted by at least one of the blades of the stack. In some embodiments, the measuring step includes using an infrared camera to generate a temperature map (e.g., a set of temperature profiles of the blades along the length of the stack). In certain embodiments, the method includes operating the infrared camera at a speed of at least 250 frames/second. In some embodiments, the razor blades are of uniform blade length and blade thickness, and the method further includes using the infrared camera to generate an infrared image having a length at least equal to the blade length and a width at least equal to twenty times the blade thickness.

In certain embodiments, the method further includes fanning the blades during the measuring step. In some embodiments, the fanning step includes applying an air jet to a surface of the stack. In certain embodiments, the applying step includes directing an air knife at the surface. In some embodiments, the air knife includes a dual air nozzle assembly.

In some embodiments, the method further includes recording a sequence of thermal images of the blades along the stack. In certain embodiments, a rate of capture of the images is adjusted with the relative movement of the stack such that each individual blade appears on at least one image.

In certain embodiments, the measuring step includes measuring the induced current. In some embodiments, the induced current is measured using a second coil. In certain embodiments, the method further includes monitoring the measured current for areas of reduced current, indicative of cracks.

In some embodiments, the method further includes focusing the induced current. In certain embodiments, the focusing step includes positioning counter-rotating field cancellation coils on both sides of the current-inducing coil. In some embodiments, the ratio of the current in each of the field cancellation coils to the current in the current-inducing coil is from about 1:5 to 3:5.

In certain embodiments, the providing step includes stacking the blades so that their cutting edges are in parallel alignment.

In some embodiments, the blades each have a thickness of less than about 85 microns. In certain embodiments, the air jet has a width that is less than or equal to the blade thickness.

Some of the methods described herein provide one or more of the following advantages.

Crack inspection can be conducted using automated techniques, minimizing the time and labor required for quality control and thus reducing the cost of the blades. The presence of cracks can be reliably determined, reducing the likelihood that finished razors will be rejected due to blade cracks.

The details of one or more embodiments of the invention are set forth in the accompanying drawings and the descrip-

DESCRIPTION OF DRAWINGS

Like reference numerals indicate like elements.

DETAILED DESCRIPTION

A number of approaches may be used to detect cracks in blades arranged in a blade stack. For example, electromagnetic energy can be applied to the blade stack, and a sensor, such as an infrared camera, can detect the temperature along one or more blades within the blade stack. When a blade includes a crack or a similar defect, the infrared camera can detect a substantial temperature gradient within the blade.

Figure 1:
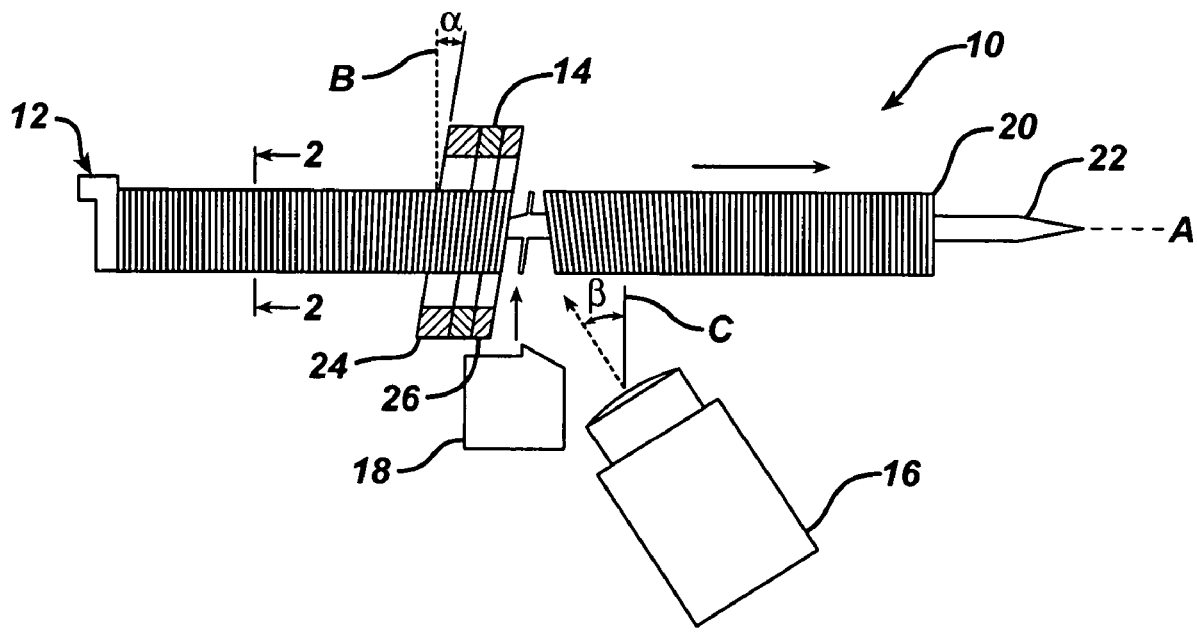
FIG. 1 is a partial cross-sectional, top view of a crack detection system.

Referring to FIG. 1, a crack detection system 10 includes a blade stack 12, an induction coil 14, counter-rotating induction coils 24, 26, an infrared (IR) camera 16, and an air knife 18. The blade stack 12 can be conveyed through the induction coil 14, which produces a current within one or more blades 20 in the blade stack 12. As a result of the current in the blades, the temperature of the affected blades generally increases. The air knife 18 forces a stream of air between blades in the blade stack 12 in order to separate one of the blades from adjacent blades. The infrared camera 16 then detects the temperature across the separated blade. A localized temperature spike detected by the infrared camera 16 can indicate the presence of a crack within the blade. An encoder measures the position of the stack (e.g., the position of blades within the stack) throughout the process. When a crack is detected, the position of the faulty blade is recorded, and the recorded position can be used to locate and remove the blade at a later stage of the process.

The blade stack 12 includes multiple razor blades 20 supported by a support fork 22. The blades 20 can be arranged in bundles of about 4000 blades/stack. The blade stack 12, for example, can have a length of about 30 cm. The blades 20 can be formed of any of various materials, such as martensitic stainless steel and/or other types of blade steel. A locking mechanism can be included on one or both ends of the support fork 22 in order to prevent substantial movement of the blades 20 along the longitudinal axis of the fork 22. The locking mechanisms, for example, can prevent the blades 20 from sliding off one or both ends of the fork 22. An example of a locking mechanism is a spring-loaded piston that is arranged to apply a controlled pressure on the end of the blade stack.

Figure 2:
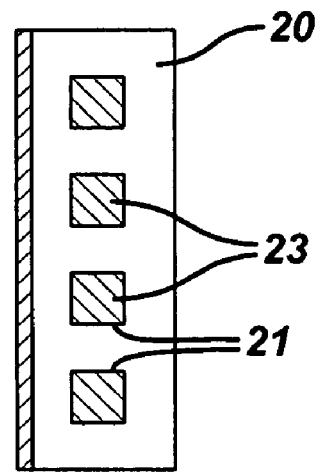
FIG. 2 is a cross-sectional view of a blade stack taken along line 2—2 in FIG. 1.

As shown in FIG. 2, the blades 20 define apertures 21 through which prongs 23 of the support fork 22 can be inserted. The apertures can be sized and shaped to fit securely around the prongs 23 of the fork 22 such that the blades 20 are substantially prevented from rotating about the prongs during the process described herein. This blade stack arrangement can help to stabilize the blades 20 during various manufacturing operations, such as coating operations, and during transportation of the blades 20. Furthermore, this blade stack arrangement can help to ensure that the blades 20 are properly oriented throughout the imaging process. Adjacent blades are typically contacting each other in the blade stack 12, but may be separated by small gaps caused by the presence of burrs and/or dust particles for example. Similarly, small gaps may be caused by a lack of flatness of one or more adjacent blades. Each of the blades 20 includes four edges (e.g., one sharp edge and three duller edges). The blades 20 also include two broad faces. The broad face of one blade can abut the broad face of an adjacent blade in the stack 12. The blades 20 can be arranged such that the sharp edges of the blades 20 are positioned along one side of the blade stack 12. In this configuration, the infrared camera 16 can detect the temperature across the blades 20 as the blade stack 12 is being conveyed in order to detect cracks within the blades 20 (e.g., cracks within interior regions of the blades, cracks within the sharp edges of the blades, and/or cracks propagating between the apertures and the sharp edges of the blades).

The blade stack 12 can be conveyed through the detection system 10 in order to identify cracks and/or other defects within the blades 20, as described in more detail below. The blade stack, for example, can be conveyed with the assistance of a computer-controlled linear motorized stage that includes a position encoder. The blade stack can be linearly displaced at a rate that allows the thermal camera to image each blade. The detection system 10 can inspect the blades for cracks at a relatively rapid rate, as compared to conventional methods (e.g., visual inspection). For example, the blade stack 12 can be conveyed and inspected at a rate of about 0.4 cm/second or greater (e.g., about 2 cm/second or greater, about 5 cm/second or greater). In certain embodiments, the blade stack 12 is inspected at a rate of about 100 blades/second or greater (e.g., about 250 blades/second or greater, about 500 blades/second or greater, about 650 blades/second or greater).

Referring again to FIG. 1, the induction coil 14 encircles the blade stack 12. The induction coil 14 can be formed of any of various conductive materials, such as copper and/or aluminum. The induction coil 14 can be connected to an energy source that generates a high frequency alternating current. Upon activating the energy source, the induction coil 14 can carry a current of about 30 Amperes to about 400 Amperes (e.g., about 150 Amperes to about 250 Amperes). Upon activating the energy source to which the induction coil 14 is connected, the induction coil 14 applies electromagnetic energy to the blade stack 12, inducing a circulating current within the blade stack 12. As a result of resistive losses, the electrical current can increase the temperature of the blade(s) 20. The temperature of the blade typically increases as the resistivity increases. It is believed that cracks within the blades create an increased resistance, and thus create a localized temperature gradient as current passes through the cracked region of the blade. The temperature differential between cracked and uncracked regions of the blades 20 can be a function of the current in the blades 20. For example, as the current in the blade increases, the temperature differential generally increases, and vice versa.

The current induced within the blade(s) of the blade stack 12 generally circulates in a direction perpendicular to the magnetic field and in the same plane as the induction coil 14. For example, the current can circulate in a plane in which the broad faces of the affected blades lie. Thus, the current does not generally flow across the blade-to-blade interfaces along the stack. This can be beneficial in detecting cracks within the blades 20, as interference created by the blade-to-blade interfaces is reduced (e.g., eliminated).

The induction coil can induce a power of about 100 Watts to about 1000 Watts in the blade stack 12. The current in each blade 20, for example, can range from about 1 Amperes to about 15 Amperes (e.g., about 1 Ampere to about 10 Amperes, about 5 Amperes). Consequently, the temperature differential between cracked and uncracked regions of the blades 20, can range from about 1° C. to about 40° C. (e.g., about 10° C. to about 20° C.). The overall temperature increase of the blade can be limited to about 50° C. or less. By limiting the temperature increase in the blades 20 to about 50° C. or less, for example, substantial damage to the blades 20 can generally be prevented.

In some embodiments, as shown in FIG. 1, the induction coil is oriented at an angle α relative to a plane B extending substantially perpendicular to a longitudinal axis A of the blade stack 12. Angle α, for example, can be about 0 degrees to about 30 degrees (e.g., about 10 degrees to about 20 degrees). As the blade stack 12 is being conveyed through the induction coil 14, air pressure from the air knife 16 can cause some of the blades 20 to tilt as they are fanned, such that they are substantially parallel to the induction coil 14 (e.g., about 0 degrees to about 30 degrees relative to the plane B extending substantially perpendicular to the longitudinal axis A of the blade stack). Adjusting the angle a so that the plane of the induction coil 14 is substantially parallel to the broad surface of the blades can increase (e.g., optimize) the efficiency of the current induction process. Furthermore, as the angle between the broad side of the blades 20 and the infrared camera's line of view (the dotted arrow in FIG. 1) approaches 90 degrees, the thermal image of cracks within the blades generally becomes more pronounced. Thus, by tilting the blades 20 as they pass through the induction coil 14, the infrared camera 16 can, in some cases, achieve a better view of the broad-faces of the blades 20 for crack detection purposes.

Using a device capable of creating non-contact induction, such as the induction coil 14, can be advantageous because the lack of physical contact between the induction coil 14 and the blades 20 can provide a substantially consistent electrical connection, as compared to contact induction. At high currents, physical contact points of contact induction devices can cause arcing, which can result in an inconsistent electrical contact. Arcing, however, can be substantially reduced or eliminated by using non-contact induction.

The counter-rotating induction coils 24, 26 are positioned on each side of induction coil 14. The counter-rotating induction coils 24, 26 can be formed of any of various conductive materials, such as copper and/or aluminum. Like the induction coil 14, the counter-rotating induction coils 24, 26 can be connected to a power source.

The counter-rotating induction coils 24, 26 deliver energy to the blade stack 12 at the same time as the induction coil 14. The counter-rotating induction coils 24, 26 carry a fraction of the current carried by the induction coil 14, and the current carried by the counter-rotating induction coils 24, 26 flows in a reverse direction relative to the current flow in the induction coil 14. The counter-rotating induction coils 24, 26, for example, can carry a counter-rotating current of about ⅕ to about ⅗ of the current carried by the main central coil. Because the counter-rotating induction coils 24, 26 are positioned on each side of the induction coil 14, the induction created by the counter-rotating induction coils 24, 26 substantially cancels a portion of the induction created by the induction coil 14. This can be particularly advantageous for non-contact induction because the energy transmitted by non-contact induction devices (e.g., induction coil 14) tends to fan out slightly. For example, the energy transmitted to the blade stack 12 by the induction coil 14 generally induces a current in those blades over which the induction coil 14 is positioned, as well as in several neighboring blades. The current induced by the induction coil 14, for example, can span over a distance of about 5 mm, which can include about 60 to about 100 blades. The counter-rotating induction coils 24, 26 can advantageously negate at least a portion of the induction created by the induction coil 14, such that a smaller area of the blade stack (e.g., fewer blades) experiences a substantial increase in induction. This, as discussed below, can help the infrared camera 16 to more easily identify temperature gradients within the blade stack 12, and thus more easily identify cracks within the blades 20.

Figure 3:
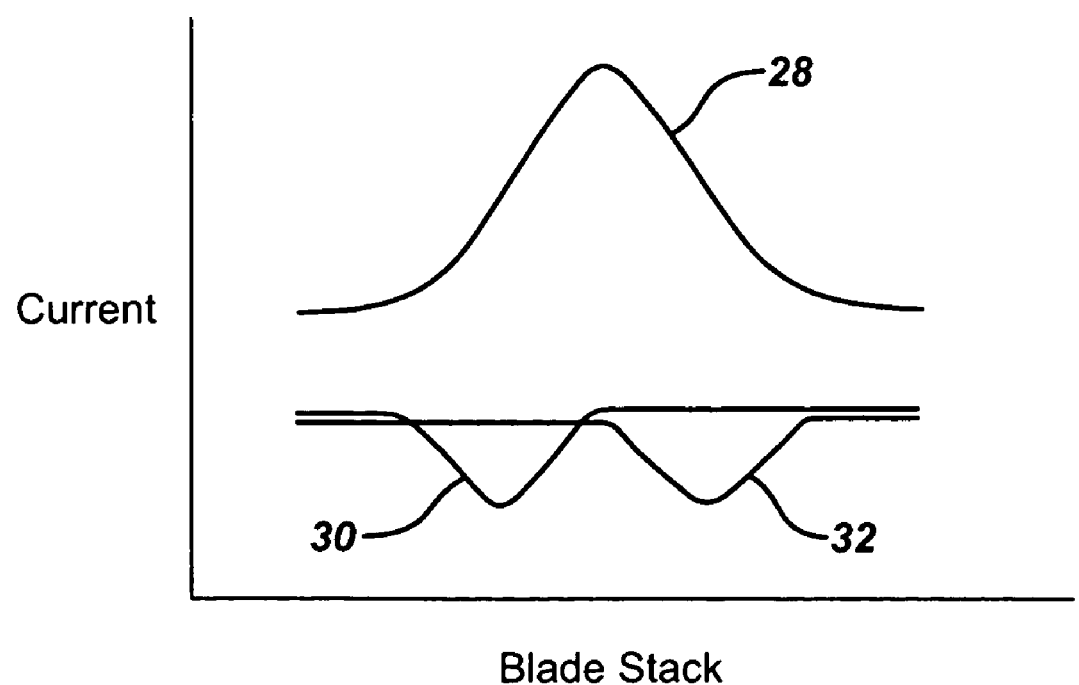
FIG. 3 is a graphic display of currents transmitted to the blade stack by an induction coil and counter rotating induction coils of the crack detection system of FIG. 1.
Figure 4:
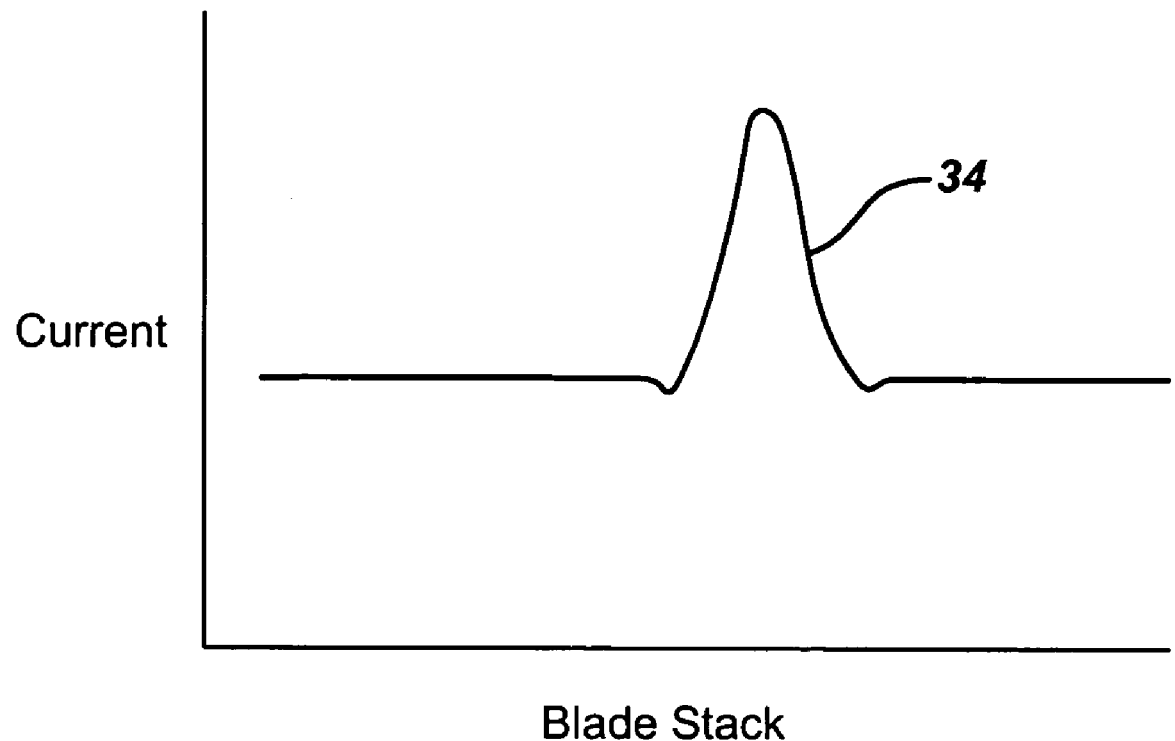
FIG. 4 is a graphic display of a current in the blade stack resulting from the induction coil and the counter-rotating induction coils.

FIG. 3 illustrates currents 28, 30, 32 produced within a portion of the blade stack 12 that is energized by the induction coil 14 and the counter-rotating induction coils 24, 26. Current 28 is produced by the induction coil 14, and currents 30, 32 are produced by counter-rotating induction coils 24, 26, respectively. The current 28 is produced primarily within blade(s) in a central region of the blade stack portion. The currents 30, 32 are produced primarily within blade(s) on each side of the blade(s) in the central region. As shown, the currents 30, 32 substantially negate the current 28 produced in the blades neighboring the blades in the central region of the blade stack portion. Referring to FIG. 4, by negating the current 28 produced in the blades neighboring the central region of the blade stack portion, a resulting current 34 is present in substantially only those blades 20 in the central region of the blade stack portion. In some cases, for example, substantially only the region of the blade stack 12 covered by the induction coil 14 carries the current 34. Because smaller regions of the blade stack 12 carry the current 34, the overall period of time that each blade carries the current can be reduced. Thus, the temperature within the blades 20 can be maintained at a relatively low temperature, which can reduce background noise created by neighboring blades and can help to prevent heat damage to the blades 20.

Referring again to FIG. 1, the air knife 18 includes a pressurized air source and an aperture through which the pressurized air can be expelled. The aperture of the air knife 18 can have a diameter or width of about 0.025 mm to about 0.075 mm. The area of the aperture, for example, can range from about 0.9 mm$^2$ to about 2.7 mm$^2$. The air knife 18 can produce an air stream having a pressure of about 550 kPa or greater (e.g., about 100 kPa to about 1000 kPa, about 500 kPa to about 750 kPa) and a relatively high velocity (e.g., about 25 m/s to about 100 m/s). The air knife 18 can be positioned from about 0.5 cm to about 2.5 cm away from the blade stack 12 in the region of the blade stack 12 in which the blades 20 are exposed to the electromagnetic energy. In some embodiments, the air knife 18 is positioned such that the air stream flows at an angle of approximately 90 degrees relative to the longitudinal axis A of the blade stack 12.

By blowing a concentrated stream of air into the blade stack 12, the air knife 18 can separate adjacent blades 20 to a predetermined distance. For example, as the blade stack 12 is being conveyed, the air knife 18 delivers a stream of air to the stack 12 that systematically flips individual blades from one side of the air stream to the other. Thus, for a period of time, the blade that is flipped from one side of the air stream to the other is separated from both adjacent blades. The blade being flipped can be separated from adjacent blades by a distance of about 2 mm or more (e.g., about 3 mm or more, about 5 mm or more). By separating one blade from adjacent blades, the air knife 18 can provide a better view for the infrared camera 16. For example, by increasing the distance between adjacent blades, the infrared camera can have a view of the blade that is substantially unobstructed or less obstructed by neighboring blades.

Alternatively or additionally, the air knife 18 can help to focus the energy from the induction coil 14 on fewer blades. For example, as the separation distance between blades increases, the number of blades affected by the narrowly focused electromagnetic energy can be reduced. In some embodiments, the energy can affect substantially only the blade that is separated from its neighboring blades by the air knife 18. As a result, interference from adjacent blades, which can negatively affect the detection of temperature gradients resulting from cracks within the separated blade, can be reduced (e.g., substantially eliminated).

The infrared camera 16 can have a spatial resolution of about 10 μm to about 100 μm (e.g., about 20 μm to about 40 μm), a temperature resolution of about 0.01° C. to about 0.5° C. (e.g., about 0.05° C. to about 0.2° C.), and a frame rate of about 60 frames/second to about 1500 frames/second (e.g., about 500 frames/second to about 1000 frames/second). The infrared camera 16 can be arranged at an angle β relative to a plane C extending perpendicular to the longitudinal axis of the blade stack, and at a distance of about 3 cm to about 30 cm from the blade stack 12. Angle β, for example, can be about 15 degrees to about 60 degrees. In the event that the field of view of the thermal camera does not cover the entire width of one blade, the measurement can be accomplished in a succession of staggered scans. The arrangement and specifications of the infrared camera 16, for example, can be selected to provide clear thermal images of the blades 20 as they are conveyed in the blade stack 12.

In some embodiments, the infrared camera 16 includes a solid-state cooled detector arranged in a focal plane. However, uncooled microbolometers can also be used. Any of various infrared cameras can be used. Examples of infrared cameras include the Phoenix-Mid imager manufactured by Flir Systems (N. Billerica, Mass.), Scan IR II manufactured by Ircon, and Mikroline 2700 manufactured by Mikron, and SBF184 focal plane array manufactured by Santa-Barbara Focal Plane (Goleta, Calif.).

The infrared camera 16 can measure the temperature of the blades 20 as they are flipped from one side of the air stream to the other. The infrared camera 16, for example, can detect temperature gradients within the blades 20. Substantially unflawed blades (e.g., blades without cracks) generally have a substantially uniform temperature gradient along the blade. However, as noted above, cracks within the blades can increase the resistance and the temperature in particular regions of the blade. Thus, temperature gradients of blades that have one or more cracks are generally not uniform. For example, such temperature gradients can include a temperature spike (e.g., a substantial increase in temperature) in the cracked region of the blade. In some embodiments, the infrared camera 16 can scan the blade stack 12 at a rate of about 1 cm/s or greater (e.g., about 4 cm/s or greater, about 8 cm/s or greater).

In certain embodiments, the temperature measurements recorded by the infrared camera can be transmitted to a display. For example, the data (i.e., the temperature measurements) can be plotted on a graph to help the user to more easily identify cracked regions of the blades. Alternatively or additionally, software can be configured to automatically detect the presence of an abnormally high temperature gradient and to record the position of the cracked blade within the stack from the position encoder reading.

Upon detecting a cracked blade, the position along the stack is read from the position encoder, recorded, and displayed to an operator. The operator can then extract the faulty blade from the stack at the later stage of the process.

While several embodiments were discussed above, other embodiments are possible.

In some embodiments, the induction coil 14 and/or the counter-rotating induction coils 24, 26 are water-cooled to reduce their active temperature. For example, water or another type of cooling liquid can be cycled through hollow passageways within the coils in order to maintain targeted temperature levels within the coils.

In some embodiments, the air knife 16 includes a dual nozzle design. For example, one nozzle can direct air to an upper region of the blade stack 12 and another nozzle can direct air to a lower portion of the blade stack 12. As a result, the air can be delivered to the blade stack 12 in a narrower stream. This can help to prevent multiple blades from being simultaneously flipped by the air stream, for example.

In certain embodiments, the detection system 10 includes a magnetic separator as an alternative to or in addition to the air knife 18. The magnetic separator can include magnets positioned adjacent the blade stack 12. As a result, magnetization can be produced within the blade stack 12. The magnets can be arranged to cause the blades 20 to repel one another. The magnetic separator can be positioned near the induction coil 14 such that the blades 20 are separated as they are conveyed through the induction coil 14.

While the embodiments described above involve transmitting electromagnetic energy to the blade stack 12 with the induction coil 14, other devices can alternatively or additionally be used to induce current in the blades 20. In some embodiments, for example, surface coils (sometimes called "pancake coils") are used to induce current in the blades 20. Surface coils have flat windings and can be positioned parallel to a side of the blade stack 12. For example, a rectangular surface coil can be positioned parallel to the side of the blade stack 12 along which the sharp edges of the blades 20 are oriented. The thermal camera can be aimed at the blades either through the aperture in the center of the coil, or through the spacings between the windings in order to image the temperature of the surface of the blades. The induced current in the blades 20 generally lies in a plane parallel to the surface coils, and generally circulates in a direction opposite the direction of the current in the surface coils.

In certain embodiments, current is induced within the blades 20 using electrically conductive rollers. For example, the detection system 10 can include a pair of conductive rollers electrically connected to a power source. The rollers can be formed of any of various conductive materials, such as copper, brass, copper-tungsten (75%), and/or silver-graphite. The rollers can have a diameter ranging from about 5 mm to about 30 mm. The rollers can be spring-loaded to contact the blade stack 12 with a predetermined force. As the blade stack 12 is conveyed, the rollers can contact one or more of the blades 20, thereby transmitting energy to the one or more blades 20. For example, the rollers can roll along opposite sides of the blade stack 12 as the blade stack 12 is being conveyed. In some embodiments, the rollers are sized and shaped to contact about ten blades or fewer (e.g., about 5 blades or fewer, about 1 blade) at a time. Thus, current can be induced in a limited number of blades along the blade stack at a given time. By limiting the number of blades induced with current at a given time, interference resulting from neighboring blades when performing the infrared scan can be substantially reduced or eliminated. Similarly, the blades can be heated for a reduced period of time, thereby reducing the risk of heat related damage.

In some embodiments, a current detector is used instead of or in addition to the infrared camera 16. The current detector can be part of a coil that is configured to encircle the blade stack 12. The encircling coil, for example, can include two series of windings. The first series of windings can be connected to an alternating power source in order to induce an eddy current in the blades 20. The second series of windings can be positioned nearer the blades than the first series of windings, and can detect the eddy current in the blades 20. Generally, the amplitude of the current signal detected by the current detector decreases in regions of the blade that are cracked. Thus, decreased amplitude in the current signal can indicate that the blade being scanned is cracked.

In certain embodiments, the current detector alternatively or additionally includes a planar array of current sensors arranged in relatively close proximity to the blade stack 12. Like the second series of windings discussed above, the planar array of sensors can detect the eddy current within the blades 20, and cracks within the blades can be detected by monitoring the current for decreases in amplitude.

While the embodiments discussed above involve the use of induction coils and/or rolling electrodes to induce current in the blade stack 12, other types of energy sources (e.g., thermal sources) can be used to impart energy to the blade stack 12. In such embodiments, the infrared camera can be used to measure the temperature across the blades. As described above, a localized temperature gradient in the blade can indicate the presence of a crack. For example, a crack within the blade may appear as a cold spot. Examples of thermal sources that can be used to impart energy to the blade stack 12 include flash lamps, laser beams, microwave generators, electrical power supplies, induction heaters, and ultrasonic generators. Thermal energy from these sources can be delivered to the blade stack 12 using any of various techniques, such as pulsed delivery, step delivery, and lock-in delivery. For pulsed delivery, the thermal energy is delivered in a short burst and the thermal measurement is performed while the blades 20 are cooling. For step delivery, the thermal energy delivered to the blade stack 12 is abruptly increased and maintained while the temperature of the blades 20 is measured. For lock-in delivery, a series of thermal energy pulses are delivered. The series of pulses can be timed with the temperature detection equipment using a lock-in amplifier to substantially eliminate the effect of noise.

Other embodiments are within the scope of the following claims.

What is claimed is:

1. A method of inspecting razor blades for cracks comprising:
    providing a plurality of razor blades in a stack,
    inducing a current in the stack, and
    measuring a parameter that is related to the current and indicative of the presence or absence of cracks in the razor blades.

2. The method of claim 1 wherein the inducing step comprises placing an induction coil adjacent the stack and delivering alternating current to the coil.

3. The method of claim 2 wherein the inducing step comprises placing the induction coil around the stack and causing relative movement between the induction coil and the stack in a direction parallel to a long axis of the stack.

4. The method of claim 1 wherein the measuring step comprises measuring the temperature of at least one of the razor blades in the stack.

5. The method of claim 4 further comprising monitoring the measured temperature for localized areas of relatively higher temperature, indicative of cracks.

6. The method of claim 4 further comprising obtaining a set of temperature profiles of the blades along the length of the stack.

7. The method of claim 1 wherein the measuring step comprises measuring infrared radiation emitted by at least one of the blades of the stack.

8. The method of claim 7 wherein the measuring step comprises using an infrared camera to generate a set of temperature profiles of the blades along the length of the stack.

9. The method of claim 1 or 8 further comprising fanning the blades during the measuring step.

10. The method of claim 9 wherein the fanning step comprises applying an air jet to a surface of the stack.

11. The method of claim 10 wherein the applying step comprises directing an air knife at the surface.

12. The method of claim 11 wherein the air knife includes a dual air nozzle assembly.

13. The method of claim 8 comprising operating the infrared camera at a speed of at least 250 frames/second.

14. The method of claim 8 wherein the razor blades are of uniform blade length and blade thickness, and the method further comprises using the infrared camera to generate an infrared image having a length at least equal to the blade length and a width at least equal to twenty times the blade thickness.

15. The method of claim 1 further comprising recording a sequence of thermal images of the blades along the stack.

16. The method of claim 1 wherein the measuring step comprises measuring the induced current.

17. The method of claim 16 wherein the induced current is measured using a second coil.

18. The method of claim 16 further comprising monitoring the measured current for areas of reduced current, indicative of cracks.

19. The method of claim 1 further comprising focusing the induced current.

20. The method of claim 19 wherein the focusing step comprises positioning counter-rotating field cancellation coils on both sides of the current-inducing coil.

21. The method of claim 20 wherein the ratio of the current in each of the field cancellation coils to the current in the current-inducing coil is from about 1:5 to 3:5.

22. The method of claim 1 wherein the providing step comprises stacking the blades so that their cutting edges are in substantially parallel alignment with one another.

23. The method of claim 11 wherein the blades each have a thickness of less than about 85 microns.

24. The method of claim 11 or 23 wherein the air jet has a width that is less than or equal to the blade thickness.

25. A method of inspecting razor blades for cracks comprising:
    providing a plurality of razor blades in a stack,
    inducing a current in the stack, and
    measuring infrared radiation emitted by at least some of the blades of the stack to determine the presence or absence of cracks in the razor blades.

* * * * *